United States Patent
Branch

(10) Patent No.: US 8,361,002 B2
(45) Date of Patent: Jan. 29, 2013

(54) ORTHOTIC APPARATUS AND METHOD FOR USING SAME

(75) Inventor: Thomas P. Branch, Atlanta, GA (US)

(73) Assignee: ERMI, Inc., Atlanta, GA (US)

( * ) Notice: Subject to any disclaimer, the term of this patent is extended or adjusted under 35 U.S.C. 154(b) by 0 days.

(21) Appl. No.: 13/018,992

(22) Filed: Feb. 1, 2011

(65) Prior Publication Data

US 2011/0218469 A1    Sep. 8, 2011

Related U.S. Application Data

(63) Continuation of application No. 12/328,539, filed on Dec. 4, 2008, now abandoned, which is a continuation of application No. 10/720,023, filed on Nov. 19, 2003, now Pat. No. 7,479,121, which is a continuation of application No. 09/779,329, filed on (Continued)

(51) Int. Cl.
*A61F 5/00* (2006.01)

(52) U.S. Cl. ........................................... 602/13; 602/27

(58) Field of Classification Search .................... 602/12, 602/23–27, 13; 128/882, DIG. 20
See application file for complete search history.

(56) References Cited

U.S. PATENT DOCUMENTS

| | | |
|---|---|---|
| 1,950,331 A | 3/1934 | Tornsjo |
| 2,543,284 A | 2/1951 | Gleason |
| 3,581,740 A | 6/1971 | Sherbourne |
| 3,780,728 A | 12/1973 | Stader |
| 3,906,942 A | 9/1975 | Lumb, Jr. et al. |
| 3,937,215 A | 2/1976 | Barthlome |
| 4,146,021 A | 3/1979 | Brosseau et al. |
| 4,291,715 A | 9/1981 | Monte |
| 4,370,976 A | 2/1983 | Wanchik et al. |
| 4,599,996 A | 7/1986 | Seith et al. |
| 4,671,258 A | 6/1987 | Barthlome |
| 4,807,606 A | 2/1989 | Hasegawa et al. |
| 4,867,140 A | 9/1989 | Hovis et al. |
| 4,960,115 A * | 10/1990 | Ranciato ..................... 602/23 |
| 5,020,515 A | 6/1991 | Mann et al. |
| 5,033,457 A | 7/1991 | Bonutti |
| 5,056,504 A | 10/1991 | Mann |
| 5,117,814 A | 6/1992 | Luttrell et al. |
| 5,219,324 A | 6/1993 | Hall |
| 5,230,335 A | 7/1993 | Johnson, Jr. et al. |
| 5,236,411 A | 8/1993 | Backman |
| 5,242,378 A | 9/1993 | Baker |
| 5,288,286 A | 2/1994 | Davis et al. |

(Continued)

FOREIGN PATENT DOCUMENTS

| | | |
|---|---|---|
| DE | 92 17 225.3 | 4/1993 |
| WO | WO 99/03440 A1 | 1/1999 |

OTHER PUBLICATIONS

Office Action dated Sep. 28, 2001 of related U.S. Appl. No. 09/779,329 (U.S. Patent No. 6,669,660).

(Continued)

*Primary Examiner* — Michael A. Brown
(74) *Attorney, Agent, or Firm* — Alston & Bird LLP

(57) ABSTRACT

An inflatable bladder position a distance from a joint is attached to an external structural support which crosses the joint but does not support it. By inflating the bladder one limb segment is forced towards the external support thereby increasing the ranges of motion of that joint. Further, the inflatable bladder has an instant release valve which, when pressed, will instantly release the pressure within the bladder. The limb is positioned intermediate the bladder and the external structural support for optimal biomechanical efficiency.

40 Claims, 10 Drawing Sheets

Related U.S. Application Data

Feb. 8, 2001, now Pat. No. 6,669,660, which is a continuation of application No. PCT/US99/18074, filed on Aug. 10, 1999.

(60) Provisional application No. 60/096,105, filed on Aug. 10, 1998, provisional application No. 60/096,104, filed on Aug. 10, 1998, provisional application No. 60/095,952, filed on Aug. 10, 1998.

(56) References Cited

U.S. PATENT DOCUMENTS

| | | | |
|---|---|---|---|
| 5,312,322 A | | 5/1994 | Santana |
| 5,313,971 A | | 5/1994 | Upshaw |
| 5,348,530 A | | 9/1994 | Grim et al. |
| 5,378,224 A | | 1/1995 | Billotti |
| 5,407,421 A | | 4/1995 | Goldsmith |
| 5,423,333 A | | 6/1995 | Jensen et al. |
| 5,425,567 A | | 6/1995 | Albecker, III |
| 5,445,602 A | | 8/1995 | Grim et al. |
| 5,453,082 A | | 9/1995 | Lamont |
| 5,514,081 A | | 5/1996 | Mann |
| 5,514,155 A | | 5/1996 | Daneshvar |
| 5,542,911 A | | 8/1996 | Cassford et al. |
| 5,730,710 A | | 3/1998 | Eichhorn et al. |
| 5,916,186 A | | 6/1999 | Turto et al. |
| 5,950,628 A | | 9/1999 | Dunfee |
| 5,951,504 A | * | 9/1999 | Iglesias et al. ......... 602/27 |
| 6,179,800 B1 | | 1/2001 | Torrens |
| 6,238,357 B1 | | 5/2001 | Kawaguchi et al. |
| 6,409,691 B1 | | 6/2002 | Dakin et al. |
| 6,572,570 B1 | | 6/2003 | Burns et al. |
| 6,589,194 B1 | | 7/2003 | Calderon et al. |

OTHER PUBLICATIONS

Office Action dated Nov. 20, 2001 of related U.S. Appl. No. 09/779,329 (U.S. Patent No. 6,669,660).

Office Action dated Feb. 1, 2005 of related U.S. Appl. No. 10/720,023 (U.S. Patent No. 7,479,121).

Office Action dated Sep. 8, 2005 of related U.S. Appl. No. 10/720,023 (U.S. Patent No. 7,479,121).

Office Action dated Oct. 10, 2006 of related U.S. Appl. No. 10/720,023 (U.S. Patent No. 7,479,121).

Office Action dated May 1, 2007 of related U.S. Appl. No. 10/720,023 (U.S. Patent No. 7,479,121).

Office Action dated Dec. 13, 2007 of related U.S. Appl. No. 10/720,023 (U.S. Patent No. 7,479,121).

Office Action dated Sep. 1, 2010 of related U.S. Appl. No. 12/328,539, filed Dec. 4, 2008.

* cited by examiner

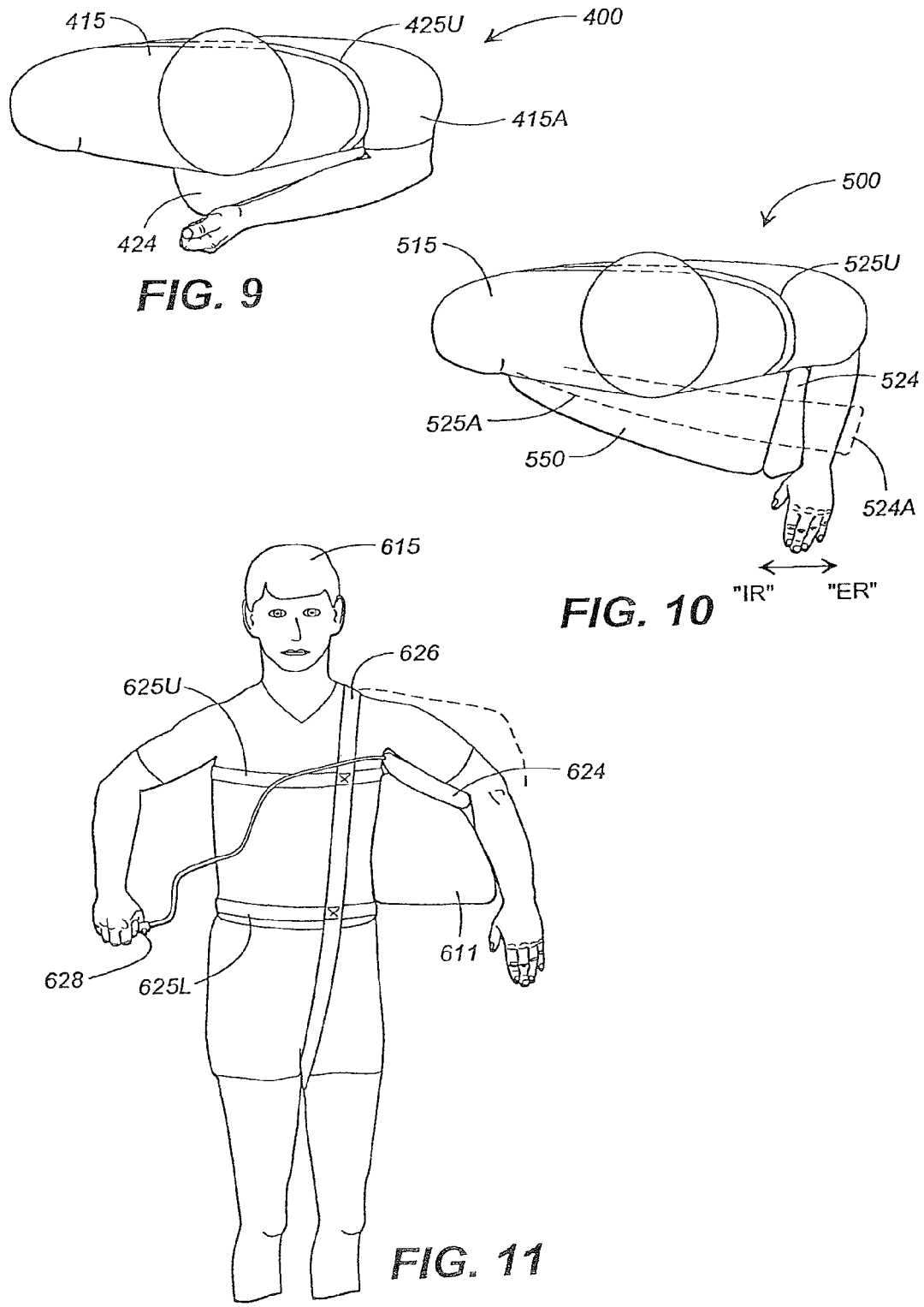

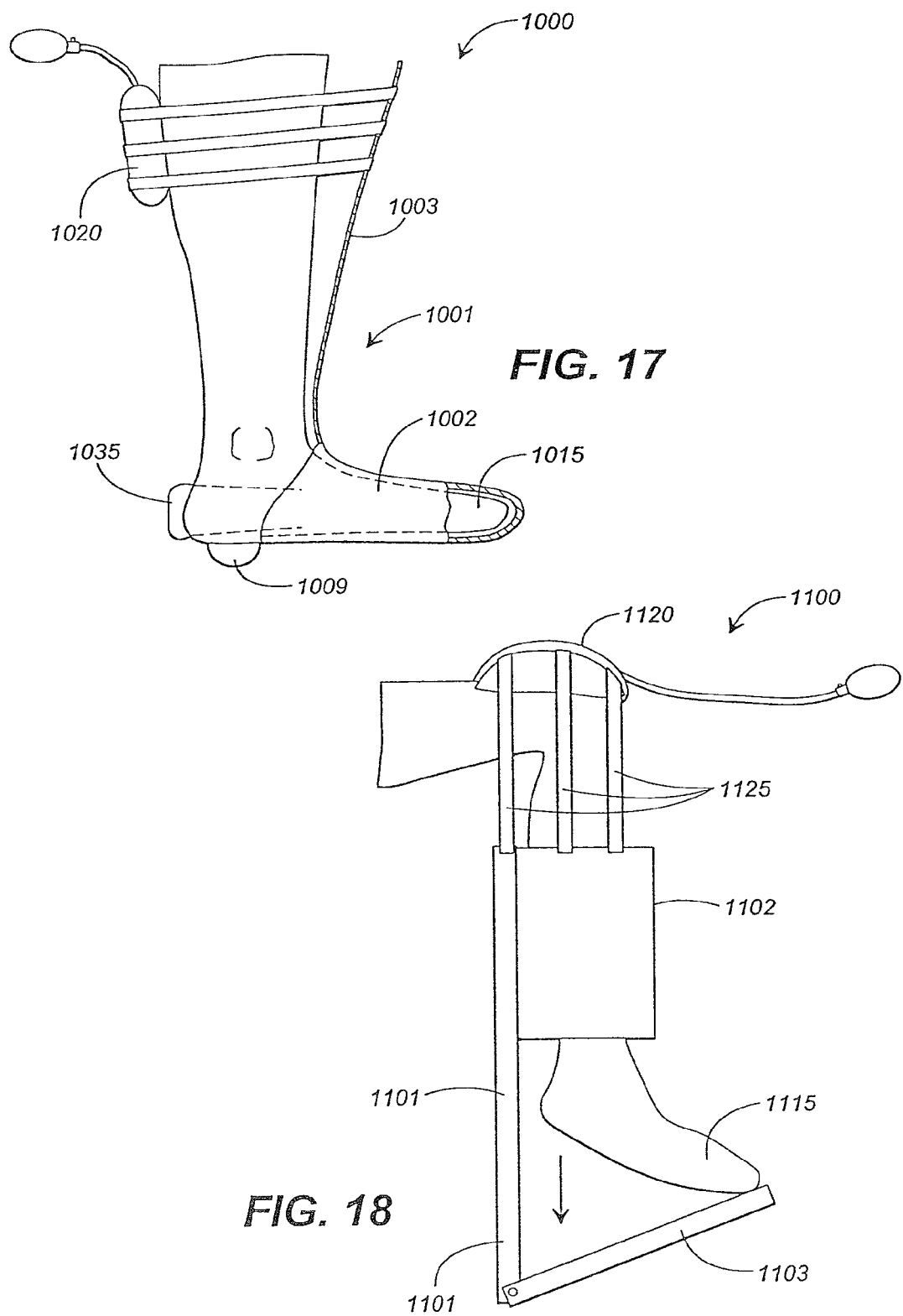

ORTHOTIC APPARATUS AND METHOD FOR USING SAME

CROSS-REFERENCE TO RELATED APPLICATIONS

This application is a continuation of U.S. Application Ser. No. 12/328,539, filed Dec. 4, 2008, now abandoned which is a continuation of U.S. Application Ser. No. 10/720,023, filed Nov. 19, 2003, now U.S. Pat. No. 7,479,121, which is a continuation of U.S. Application Ser. No. 09/779,329, filed Feb. 8, 2001, now U.S. Pat. No. 6,669,660, which is a continuation of PCT/US99/18074, filed on Aug. 10, 1999, and claims priority to U.S. Provisional Application No. 60/096,105, filed Aug. 10, 1998, U.S. Provisional Application No. 60/096,104, filed Aug. 10, 1998 and U.S. Provisional Application No. 60/095,952, filed Aug. 10, 1998. The present application claims the benefit and priority of all applications noted above, which are incorporated in their entirety hereby by reference.

TECHNICAL FIELD

This invention relates generally to orthotic devices and more particularly to orthotic devices designed to promote an increase in range of motion in a joint by the use of selectively inflatable and deflatable bladders.

BACKGROUND OF THE INVENTION

When a joint is injured either by trauma or by surgery scar tissue can form which prevents full range of motion of that joint. Obviously, this is a disadvantageous condition and should be corrected if possible. Often, such correction involves an attempt by the injured or those assisting the injured to gradually (often over a period of months) manipulate the joint so that full range of motion is eventually achieved.

Full range of motion of a joint depends upon the anatomy of that joint and on the particular genetics of each individual. Typically, joints move in two directions, flexion and extension. Typically, flexion is to 'bend the joint and extension is to straighten the joint; however, in the orthopedic convention some joints only flex. For example, the ankle has dorsiflexion and plantarflexion. Other joints not only flex and extend, they rotate. For example, the elbow joint has supination and pronation, which is rotation of the hand about the longitudinal axis of the forearm placing the palm up or the palm down.

There is a need for a class of orthotics which promote an increase in range of motion of the joint rather than to merely provide support. One such series of devices is called the Joint Active System, Inc. It combines a traditional orthotic with limb cuffs on each limb segment and a special hinge joint connecting the two cuffs. This special hinge joint has a ratchet system which allows the hinge to be sequentially bent or straightened with a special wrench or knob. If the cuffs are attached to each limb segment and the hinge is slowly bent then the joint is typically forced into flexion. Similarly, if the hinge is slowly straightened after being strapped on a bent joint, the joint is also straightened. This system relies upon the patient to strap a cuff on to each limb segment. This is difficult to do particularly if the joint to be treated is the arm needed to strap the brace. Furthermore, the pressure on each limb segment by each cuff is very painful as the joint is bent or straightened. Lastly, the ratchet system does not allow for instant release of the pressure used to force an increase in the range of motion.

Another series of devices is made by Dynasplint Inc. These devices are similar to the Joint Active System in that there is a cuff for each limb segment and a special hinge designed to promote an increase in range of motion. With the Dynasplint system, the hinge contains a special set of springs that, when tightened, will put a low load of pressure on the cuffs to bend or straighten. The same objections apply to the Dynasplint as they do to the Joint Active System. The cuffs are uncomfortable, the device is hard to put on and there is no instant release of the pressure. With this system the device must be worn for hours at a time to be effective.

There are other devices available which use inflatable bladders around a joint. They tend to use the bladder(s) to provide support across the joint. Such inflatable bladders are positioned across the joint or in near proximity to the joint.

Such conventional orthosis devices may be designed for support across a joint. In general an orthosis connects one limb segment to another across a joint. The connection is either a rigid member or a hinged joint. In this way orthotics work to support the joint as a means of protecting it. General reference is made to U.S. Pat. Nos. 5,542,911, 5,378,224, 5,348,530, and 5,730,710.

One particular device which uses the bladder(s) to provide support across the joint is also shown in U.S. Pat. No. 5,514,081 to Mann, which uses the inflatable bladder to cross the elbow joint to provide support for an elbow with a flexion contracture (the elbow joint can not fully extend). This device places the inflatable bladder across the joint so that when it inflates it holds the elbow in full extension. This device does not appear to include rigid structural members. Further, it does not isolate the bladder distant to the joint, thus maximizing the biomechanical forces across the joint for promoting elbow extension.

U.S. Pat. No. 3,581,740 has an air bladder which crosses multiple finger joints of a hand as well as the wrist. Upon inflation, the hand is moved to a normally extended, spaced apart, condition.

Some prior art patents use inflatable members to gain range of motion in the hand. U.S. Pat. No. 4,671,258 uses a cyclical therapeutic joint exerciser by inflating a pouch that crosses the joint and a spring steel insert that automatically bends the joint when the inflatable pouch is not inflated. U.S. Pat. No. 4,807,606 uses bladders around the joints in the 3 hands to exercise the joints. That is to say, the bladders are inflated and deflated sequentially with a pump device to flex and extend hand joints.

U.S. Pat. No. 5,056,504 uses the inflatable bladder in the palm against a rigid structure to push the fingers into extension. However, this U.S. Pat. No. 5,056,504 patent includes a bladder which "crosses the joint", which is not only potentially painful to the user if the joint has undergone surgery, but is not optimally biomechanically efficient in the distribution of forces as will be described later with respect to applicant's invention.

Therefore, it may be seen that there is a need in the art to provide an improved orthotic device, which can be used to straighten ("orthoun" means to straighten) limbs or joints. Therefore, it may be seen that there is a need in the art for an orthotic device and method of using same which provides optimal biomechanical distribution of load.

BRIEF SUMMARY OF THE INVENTION

The present invention overcomes deficiencies in the prior art by providing an improved orthotic device.

Generally described, the present invention comprises a strap, an inflatable member including an inflatable bladder, the inflatable member being spaced from the joint, and a device for inflating and deflating the inflatable member such that as the inflatable member is inflated, the strap is placed in increasing tension and the joint is moved.

More particularly described, the present invention comprises a structural body portion, an inflatable member, a flexible strap configured to be attached intermediate the structural body portion and the inflatable member, and an inflating device for inflating the inflatable member so that it increases in size, such that as the inflatable member is inflated, the inflatable member tend to push against the limb such that the limb is urged towards said structural body portion and the joint is moved. Other inventions are also included.

It is a further object of the present invention to provide an orthotic device which provides an optimal biomechanical application and distribution of load.

It is a further object of the present invention to provide an improved orthotic device which is easy to use.

It is a further object of the present invention to provide an improved orthotic device which is simple to manufacture. It is a further object of the present invention to provide an improved orthotic device which applies no direct pressure on the joint itself.

It is a further object of the present invention to provide an improved orthotic device which is cost-effective to manufacture and use.

It is a further object of the present invention to provide an improved orthotic device which is efficient in its use of forces.

It is a further object of the present invention to provide an orthotic device which has increased reliability.

It is a further object of the present invention to provide an orthotic device which is easy to apply and remove.

It is a further object of the present invention to provide an orthotic device which allows for instant release of pressure. It is a further object of the present invention to provide an orthotic device which provides a high load application It is a further object of the present invention to provide an orthotic device which provides an efficient load application. It is a further object of the present invention to provide an orthotic device which applies comfortable pressure.

It is a further object of the present invention to provide an improved orthotic device which is light in weight and easy to transport.

It is a further object of the present invention to provide an improved orthotic device which can be used in conjunction with a crutch for structural support.

Other objects, features, and advantages of the present invention will become apparent upon reading the following detailed description of the preferred embodiment of the invention when taken in conjunction with the drawing and the appended claims.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

FIG. 1 is a front view of a knee extension assembly 10 and ankle support member 30 used in conjunction with a conventional crutch 12.

Figure 7:
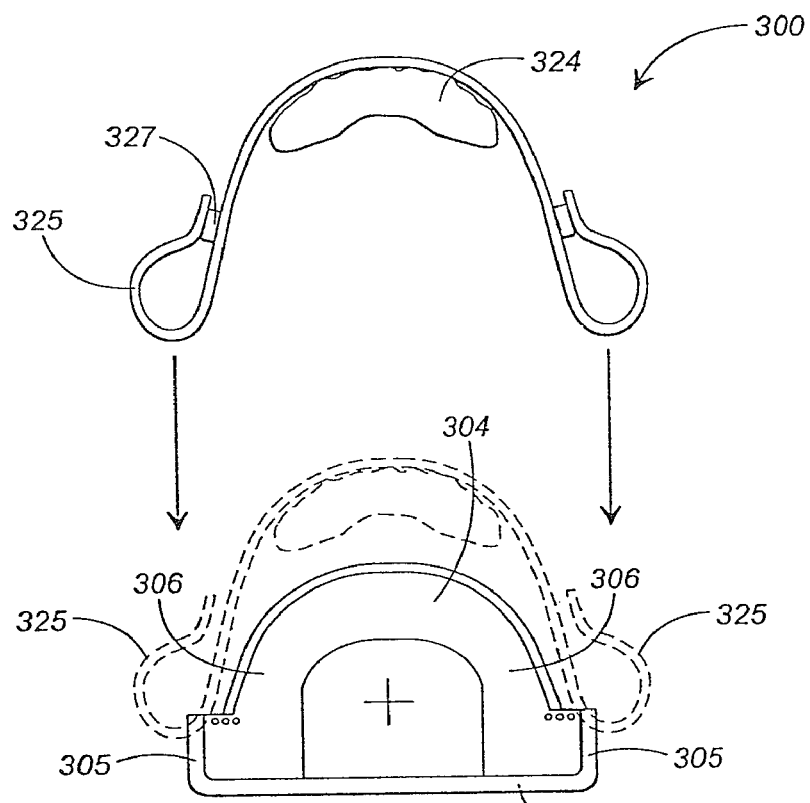

FIG. 7 is an exploded, illustrative, view of the device 300 of FIG. 7, with the portion comprised of the straps 325 and the inflatable member 324 (which includes an air bladder within a fabric pouch) detached from the main body of the device 300.

Figure 8:
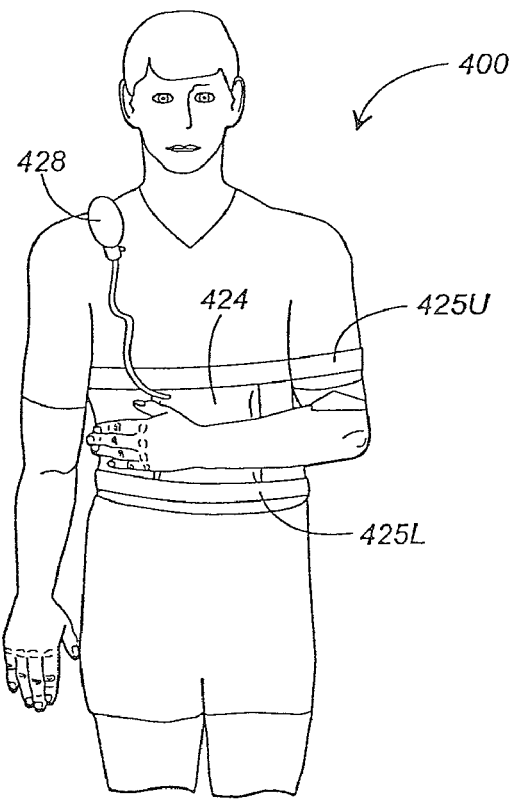

FIG. 8 is a front view of a fourth embodiment of the invention, being an apparatus 400 used in conjunction with a user 415, to provide external rotation of the shoulder.

FIG. 9 is a top view of some of the elements of FIG. 8.

FIG. 10 is a top view of a fifth embodiment of the present invention, being a device 500 which provides external rotation of the shoulder in a different range.

FIG. 11 is a front view of a sixth embodiment of the present invention, being a device 600 which provides abduction of the shoulder.

Figure 12:
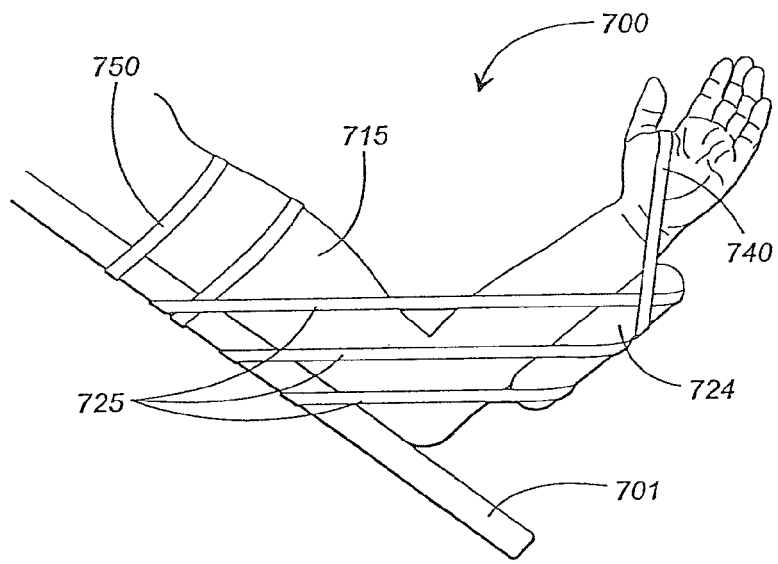

FIG. 12 is a side view of a seventh embodiment of the present invention, being a device 700 for flexion of the elbow.

Figure 13:
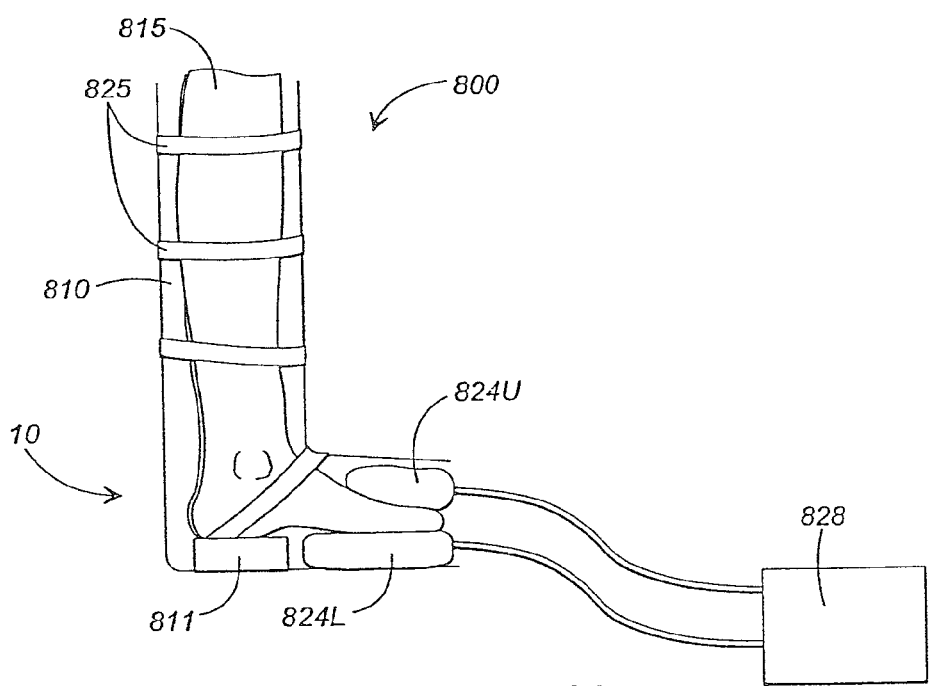

FIG. 13 is a side view of an eighth embodiment of the present invention, being a device 800 which promotes both dorsiflexion and plantarflexion alternately and continuously.

Figure 14:
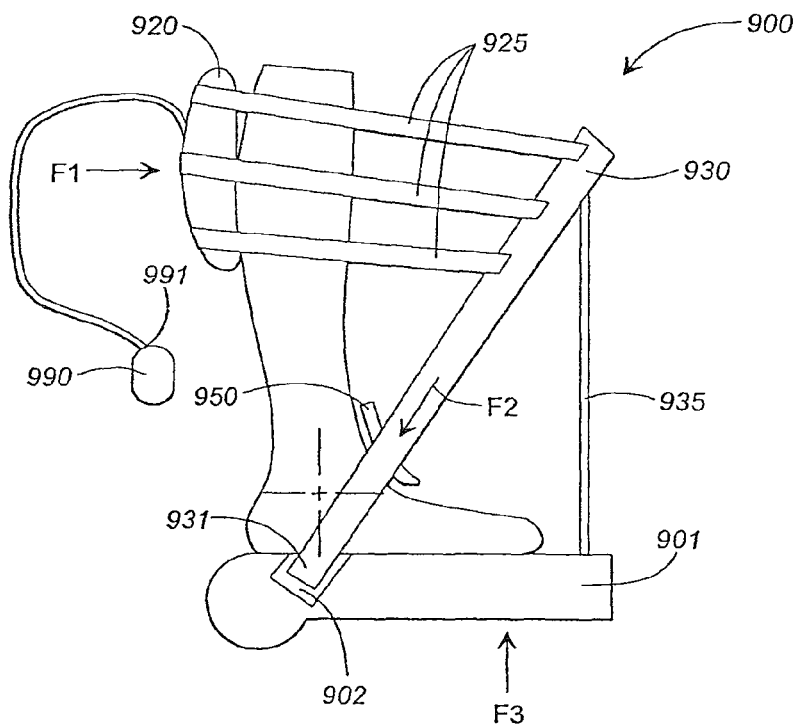

FIG. 14 is a side view of a ninth embodiment of the present invention, being a device 900 which provides dorsiflexion of the ankle joint by capturing the foot and using the inflatable member to pull the ankle into dorsiflexion. This apparatus 900 includes a substantially flat base 901, an inflatable member 920, and an including floating yoke member 930 which captures the foot as described in further detail below.

Figure 15:
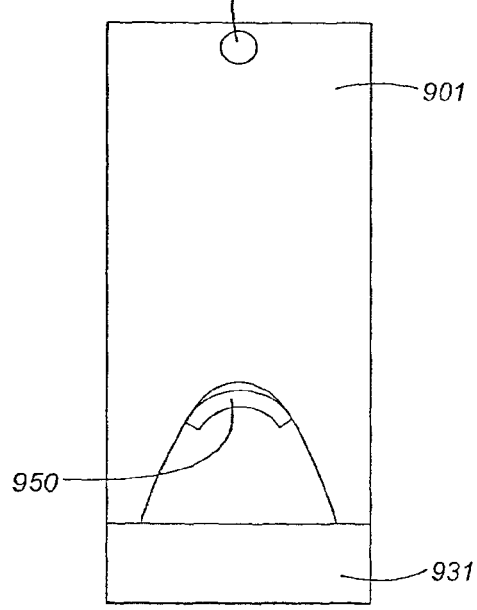
Figure 16:
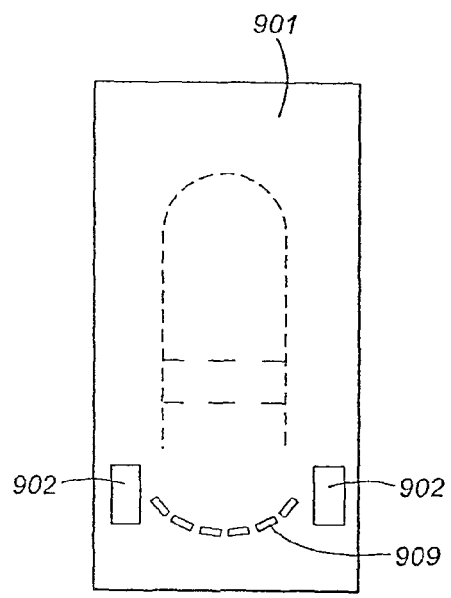

FIGS. 15 and 16 are rear elevational and top plan views, respectively, of portions of the device of FIG. 14.

FIG. 17 is a side view of a tenth embodiment of the present invention, being a device 1000 which provides dorsiflexion of the ankle joint by capturing the foot and using the inflatable member 1020 to pull the ankle into dorsiflexion. This device 1000 includes a substantially rigid structural member 1001 which resembles a open-backed "slipper" portion 1002 with a front vertical flange 1003 which extends upwardly from the top of the slipper portion and along the front of the shin of the wearer 1015.

FIG. 18 is a side view of an eleventh embodiment of the present invention, being another orthotic device 1100 which can be used to provide dorsiflexion of the ankle This device 1100 includes a base 1101, a cuff 1102 fixed to the base, a selectively positionable foot plate 1103, an inflatable member 1120, and connecting straps 1125.

Figure 19:
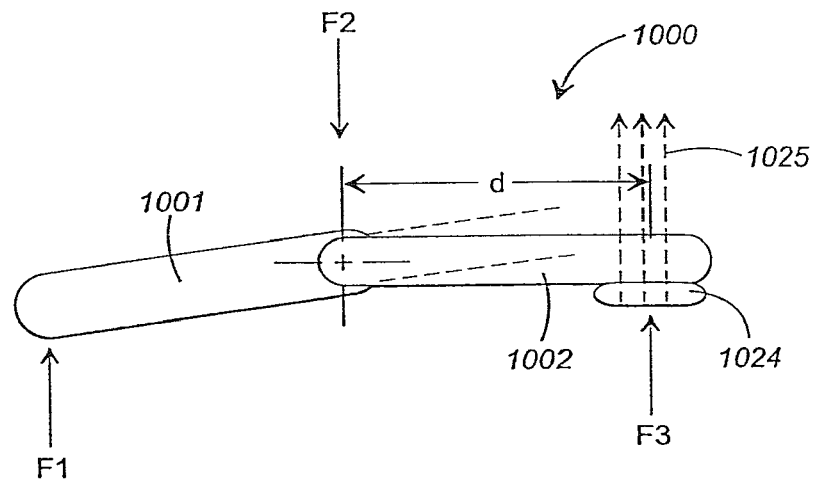

FIG. 19 is an illustrative view 1200 of a pair of exemplary limb members (such as an upper and lower, leg, or such as an upper and lower arm), and how such members can be captured by the "three point" force configuration described above. Such an inventive configuration provides an optimally efficient biomechanical application of force by positioning the inflatable member as far as possible from the pivoting point, whether that pivoting point be the joint (as shown in the FIG. 6), or the interface between the limb and the structural member (see FIG. 2).

Figure 20:
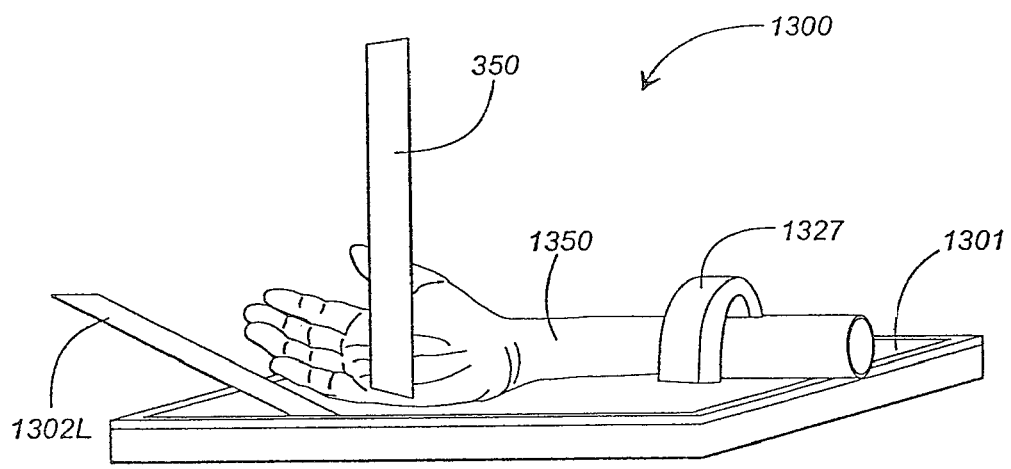
Figure 21:
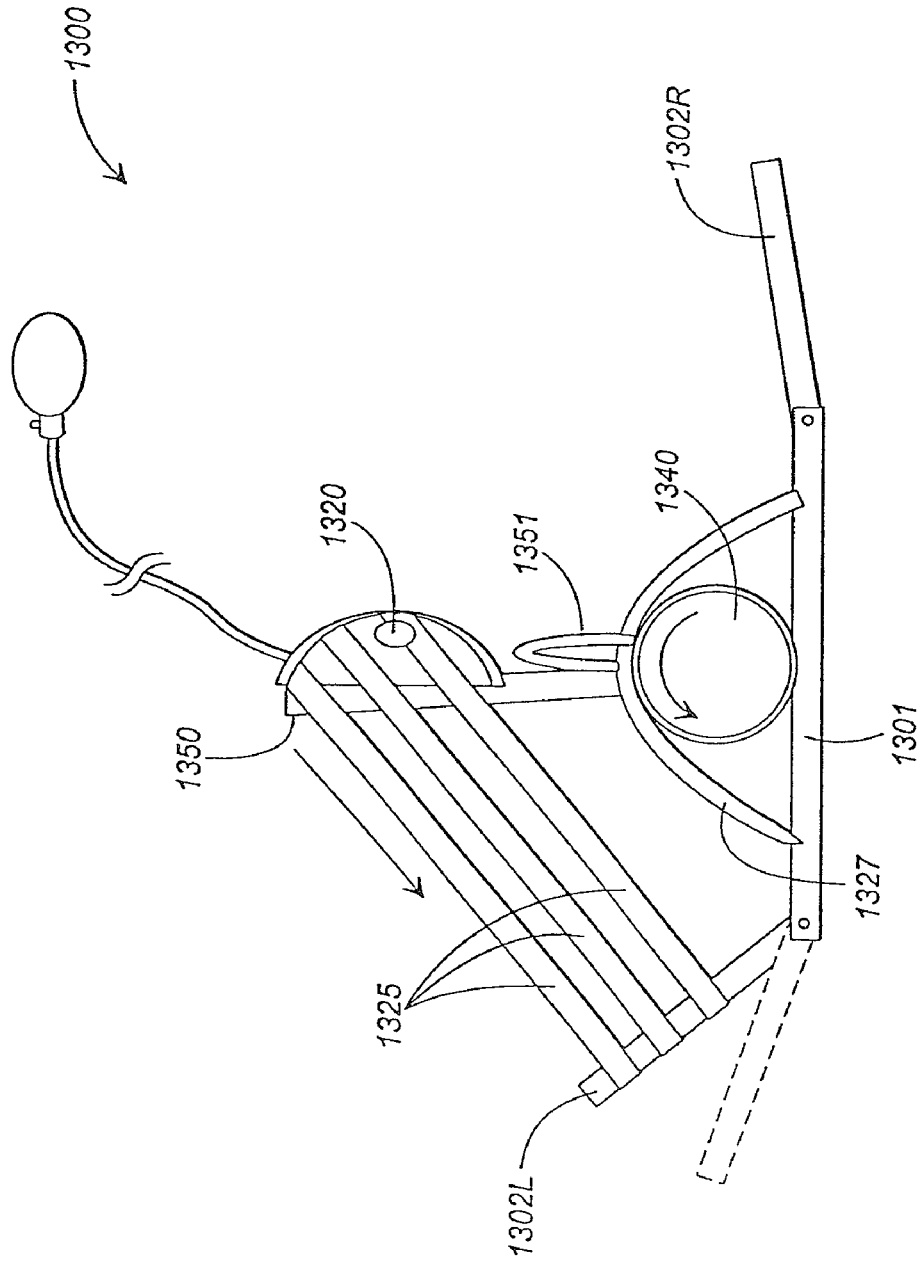

FIGS. 20 and 21 are pictorial and end views, respectively, of a forearm supination and pronation device 1300 which includes a base 1301, right and left adjustable base flanges 1302L, 1302R, respectively, an inflatable member 1320, straps 1325, a retaining cuff 1327, and a glove assembly 1350 including a thumb retainer 1351

DETAILED DESCRIPTION OF THE INVENTION

The present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

Reference is now made to the Figures, in which like elements indicate like elements throughout the several views.

The application will be discussed by reference to several different embodiments, which may share inventive concepts or alternately may each include individual inventive concepts.

First Embodiment

FIGS. 1-4

Figure 1:
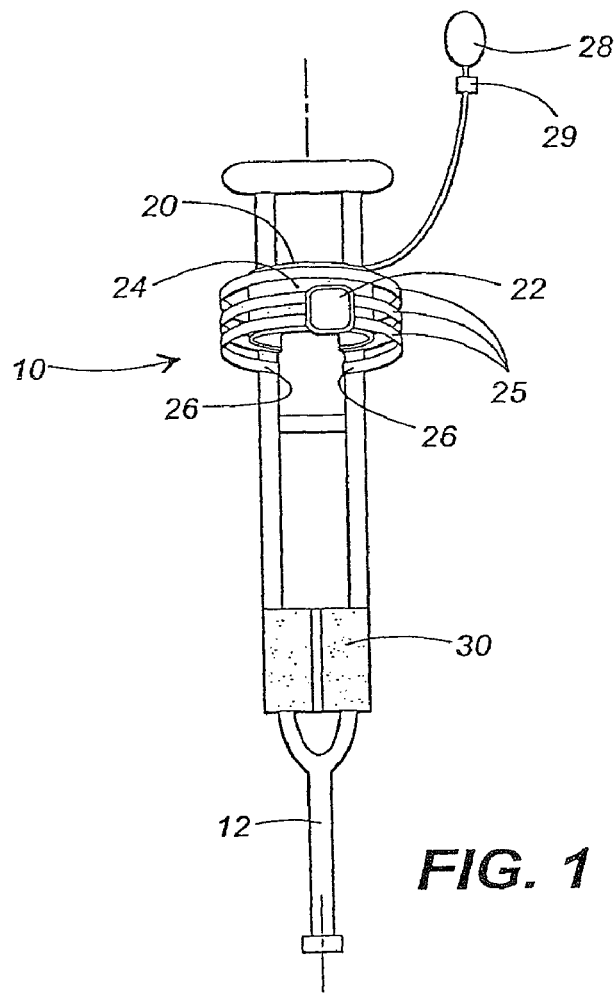
Figure 3:
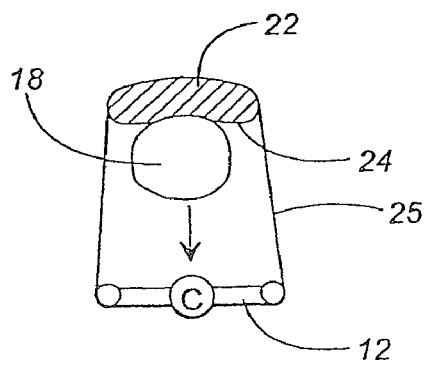
FIG. 3 is a top cross-sectional view taken transverse to the longitudinal axis of the crutch and the wearer's leg of FIG. 2, with the cross-section taken through the inflatable air bladder 22 and its containing pouch 24.
Figure 4:
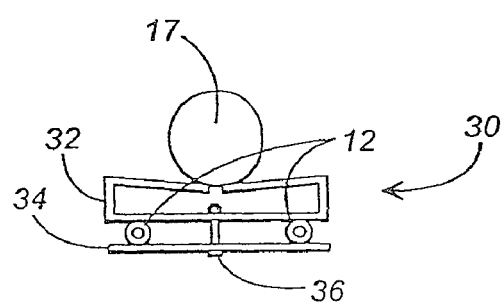
FIG. 4 is another transverse cross-section taken from the FIG. 1 configuration, but this time the cross-section is taken just above the ankle support member 30.
Figure 2:
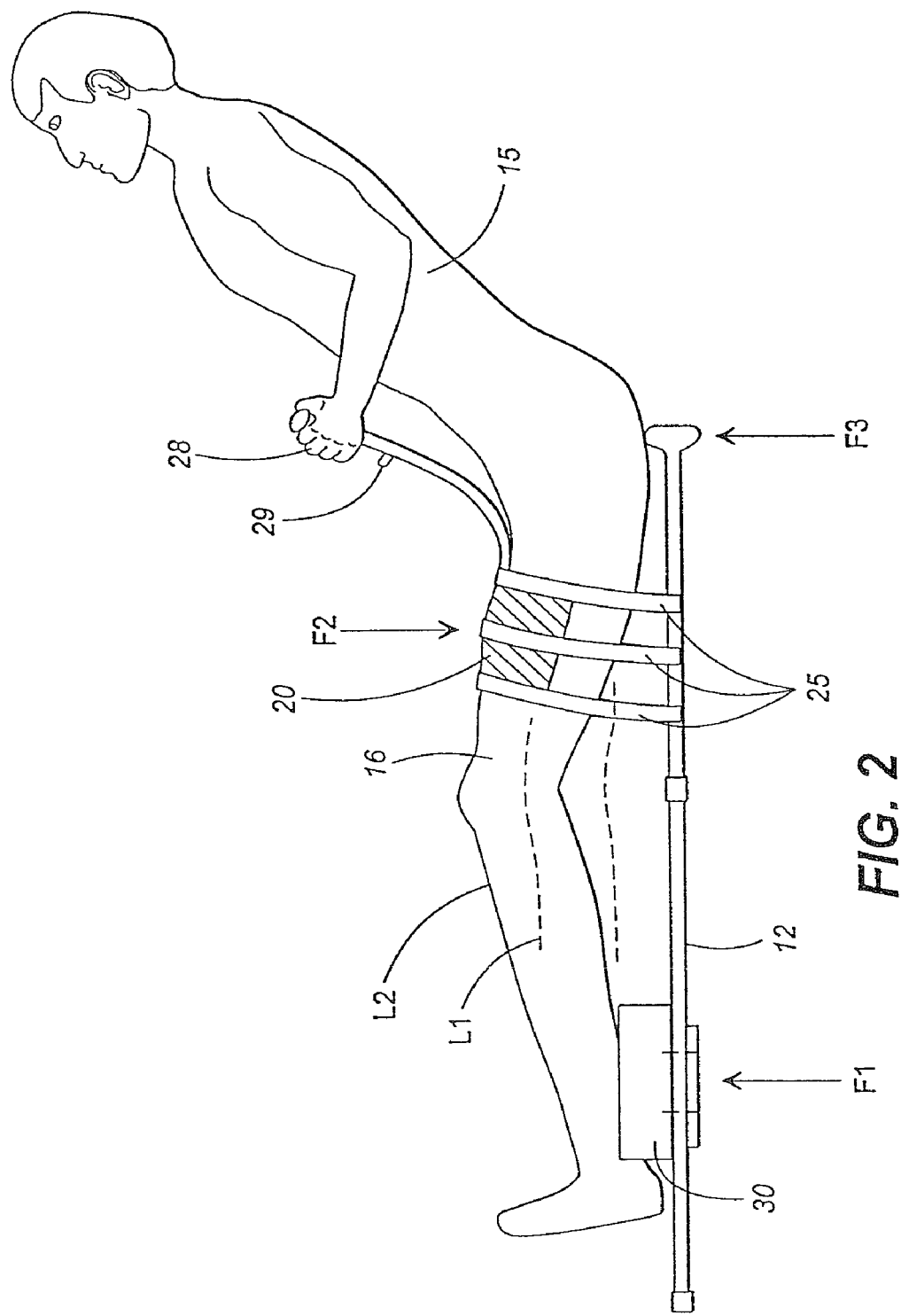
FIG. 2 is a is a side view of the elements 10, 12, being used by a wearer 15.

FIG. 1 is a front view of a knee extension assembly 10 and an ankle support member 30 used in conjunction with a conventional crutch 12. FIG. 2 is a is a side view of the elements 10, 12, 30 being used by a wearer 15. FIG. 3 is a top cross-sectional view taken transverse to the longitudinal axis of the crutch and the wearer's leg of FIG. 2, with the cross-section taken through the inflatable air bladder. FIG. 4 is another transverse cross-section taken from the FIG. 1 configuration, but this time the cross-section is taken just above the ankle support member 30.

The crutch as shown in FIG. 1 is a conventional type of crutch, which is a distinctive aspect of the present invention in that conventional crutches are readily available within the market. The present invention particularly adds the use of a knee extension assembly 10 and an ankle support member 30.

The knee extension assembly 10 includes an inflatable member 20, a plurality of straps 25, and a conventional hand operated pump 24 with a bleed valve 29. The inflatable member 20 can include an inflatable bladder 22 contained within a fabric pouch 24. The inflatable bladder 22 can, as in other configurations described herein, may be inflated by the conventional hand-operated pump 24 and deflated by use of the bleed valve 29. The plurality of straps 25 as shown in FIG. 2 can position the leg between the inflatable member and the crutch, while containing and attaching the inflatable member relative to the crutch. The configuration shown in FIGS. 1-2 includes three straps. However, other strap or bladder configurations may be used as known in the art.

The ankle support member 30 includes a cradle portion 32 and a back portion 34 is attached to the crutch towards the lower end of the crutch by use of conventional fasteners such as 36, although any suitable attachment of the ankle support member 30 to the crutch is suitable. The cradle portion 32 defines a generally upwardly (as FIG. 4 is viewed) cradle which is configured to accept a length of the leg of the user.

Upon inflation of the inflatable member inflatable member 20, it may be understood that a "three point" force combination is provided which allows for effective extension of the knee by use of an optimal, highly efficient but comfortable biomechanical application of load. This three point contact configuration is illustrated in FIG. 2 by the force arrows "F1", "F2", and "F3". Force arrow "F1" illustrates force provided upwardly on the leg by the ankle support member 30. The force arrow "F2" illustrates force provided downwardly on the leg atop the thigh of the leg by the inflatable member 20 of the knee extension assembly 10. It may be understood that this force is translated to the crutch through tension in the straps 25. The force arrow "F3" illustrates force provided upwardly on the leg by the upper end of the crutch (which may be the padded underarm rest). This three point action is further described elsewhere in this application with reference to FIG. 19.

It should be understood that although FIG. 2 illustrates the use of the air bladder atop the thigh, alternate locations of the air bladder are likewise contemplated; the inflatable bladder could alternatively be placed upon the knee, or the tibia. However, the present invention contemplates adjustability of the location of the knee extension assembly 10 along the length of the crutch, as at times (for example at the beginning of treatment) the knee joint may be sensitive to contact, and thus the knee extension assembly 10 may be adjusted so it is atop the thigh. At the same time, biomechanically the knee is a desirable location for application of the load, so later in treatment, when the knee is not as tender, the knee extension assembly 10 may be adjusted so it is atop or at least closely adjacent the knee.

Under one configuration of the present invention, the ankle support member 30 will remain at least temporarily attached to the crutch during its normal use. The patient can use the crutch in the conventional manner, with the assembly 10 carried therewith on the crutch if so desired. When an orthotic session is desired, the patient will then typically sit on a chair with the upper (underarm) portion of the crutch positioned beneath the relevant buttock. The remainder of the elongate crutch is positioned relatively underneath the length of the patient's leg, with the ankle support member 30 portion being positioned under the patient's ankle The device 10 is then attached to its position as shown in FIG. 2, and the adjustable straps are adjusted to a comfortable tension. The bladder is then filled as desired, with pressure relief being available as desired.

The straps are adjusted to provide some initial amount of pressure, with the final amount of pressure and resulting force being provided by the air. It should also be understood that the adjustability of the straps accommodates various knee positions; it should be understood that during the initial stages of recovery, the leg may not be able to be bent very much at the knee, whereas towards the end of the recovery period, the leg preferably may be bent substantially straight at the knee.

It should be understood that one portion of the present invention includes the use of straps including hook-and-loop (such as VELCRO) attachment which allow for a "take-up" feature; this feature allows for the combination of large motions of the limb. However, other take-up configurations may be used such as known in the art, such as friction or other buckles, without departing from the spirit and scope of the present invention. This applies throughout this discussion.

As noted above, the knee extension assembly according to the present invention is contemplated for use in conjunction with a conventional crutch member such as known in the art and conventionally available. It should be understood that such a crutch configuration could also be a special crutch specially configured to work with the orthotic device according to the present invention, or could simply be a straight board or other elongate structural member.

Second Embodiment

FIG. 5

Figure 5:
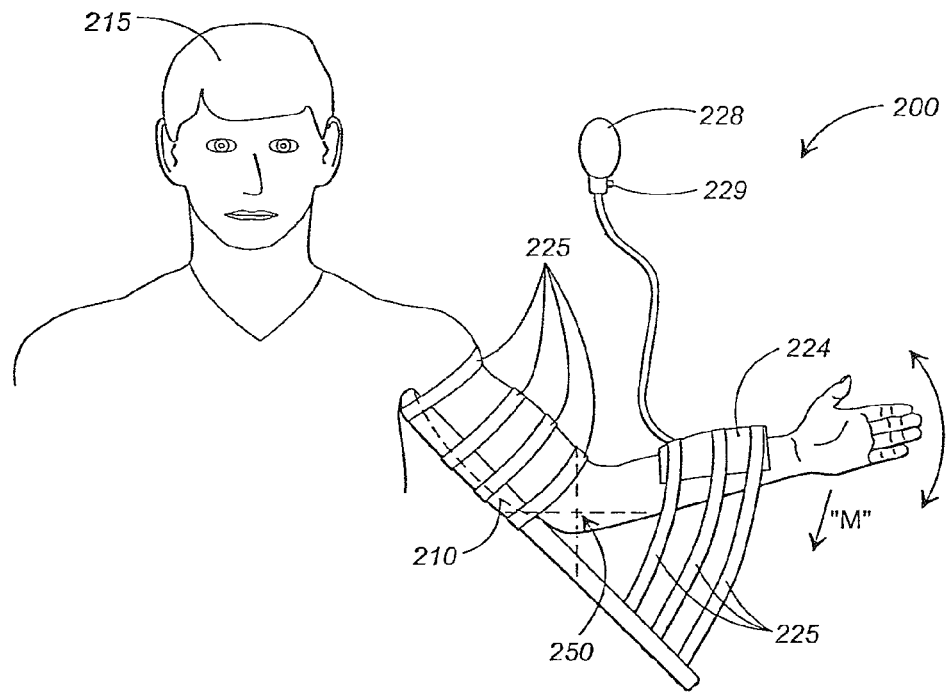
FIG. 5 shows a front view of a second embodiment 200 of the invention, being an arm orthotic device.

FIG. 5 illustrates the use of a rigid plastic or other suitable material, to provide an elongate structural member 210 which may be attached to the underside of the arm, with its lower end extending beyond the elbow, terminating in a "free end". Approximate this "free end" are attached three (as shown) straps 225 which connect an inflatable member 220 (an air bladder in a fabric pouch) to the free end of the elongate member. This member 220 is configured to be positioned adjacent to the forearm of a wearer, such that inflation of the air bag therein tends to provide pressure causing movement such as shown as M. This is conventionally called "extension" and is desired in certain types of orthotics.

It should be understood that this FIG. 5 configuration includes the "three point" force combination as described above. However, this FIG. 5 configuration is similar to the FIGS. 6 and 7 configuration, and the "three point" force configuration will be described in more detail in reference to FIG. 6.

Third Embodiment

Figure 6:
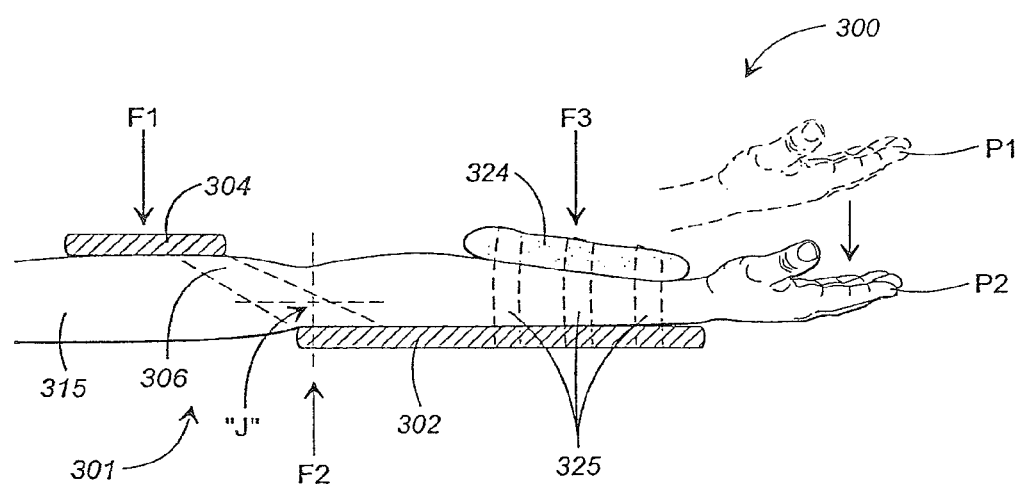
FIG. 6 is a side view of a third embodiment 300 of the present invention, being an orthotic device for extending the forearm relative to the upper arm from position P1 to position P2.

FIGS. 6 and 7

FIGS. 6 and 7 show a third embodiment of the present invention, being an apparatus 300 configured to be attached to the arm of a wearer 315. It should be understood that FIG. 6 is a more simplified version.

The apparatus 300 includes a substantially rigid structural frame 301 including a forearm bearing portion 302 and an upper arm bearing portion 304, connected by one or more connecting members 306. Also included are straps 325 and an inflatable member 320, which can include an inflatable bladder contained by a fabric pouch. As are other configurations discussed herein, the straps are sewn to the fabric pouch by conventional means. As elsewhere in this discussion VELCRO-type attachments at 327 may be provided for detachability and adjustability of the straps.

Flanges 305 (see FIG. 7) may be optionally used if desired to extend upwardly on either side of the main body to contain the forearm as desired.

FIG. 7 shows the embodiment in slightly more detail than FIG. 6. In FIG. 7, the forearm bearing portion 302, the upper arm bearing portion 304, and two connecting members 306 are shown; it may be understood that in the FIG. 7 version shown they are all part of an essentially one-piece frame which in the preferred embodiment is plastic. It should be understood that the upper arm bearing portion is contoured to conform somewhat to the upper surface of the upper arm for comfort purposes when bearing downwardly thereon.

The frame 301 of the apparatus can be plastic, wood, metal, a metal/fabric sling, or other material(s) suitable to provide the needed structural support. It should be understood that the members 302 and 305 of the frame 301 could be rigidly attached together by virtue of being part of an integral, one-piece unit, or alternately could be part of a multiple-part device which allows for relative adjustment between the members 302, 304 as desired.

As shown in FIG. 6, it may be seen that the "three point" force configuration is again utilized in this embodiment, as shown by force arrows "F1", "F2' and "F3". Force arrow "F3" illustrates the force down by the inflatable member. Force arrow "F2" illustrates the force up by forearm bearing portion 302. Force arrow "F1" illustrates the force down by upper arm bearing portion 304.

It should be understood that during the initial stages of recovery, the elbow may not be able to accommodate much pressure, and for that reason the elbow may be placed off the forearm bearing portion 302. However, towards the end of the recovery period, the elbow may be placed on the forearm bearing portion 302 for optimal biomechanical application of force.

Fourth Embodiment

FIGS. 8 and 9

FIGS. 8 and 9 show an apparatus 400 which may not include any substantially rigid members (although one against the stomach may be used), but includes the use of an inflatable member 424 and a pair of straps 425U, 425L (upper and lower), together which are configured to provide external 3 rotation of the shoulder. The upper strap 425U may be passed around the upper torso and arm of a user, leaving the opposite arm free. The lower strap 425L may be provided around the lower torso of the wearer, such as would a conventional belt. Between the upper and lower straps are attached an inflatable member 424 (being a bladder within a pouch), having its upper edge attached to the upper strap, and its lower edge attached to the lower strap, with the air bladder therein configured to be inflated and deflated as noted before.

To utilize the apparatus, the forearm is placed adjacent the air bladder, and the upper strap 425U is provided in a suitably taut configuration to keep the relevant upper arm against the wearer's side for optimal biomechanical effect. The air bladder is then inflated, causing external rotation of the shoulder. As may be understood, when desired, the air bladder may be deflated as needed, in order to remove the device, or in order to alleviate pain.

It should be understood that other configurations are also contemplated for maintaining the upper arm against the side of the user, such as but not limited to a cuff (not shown) to contain the arm but allow it to rotate as it is strapped to the body.

Fifth Embodiment

FIG. 10

As shown in FIG. 10, the two-strap apparatus as shown 2 in FIG. 7 may be complimented with a foam block or wedge 550 to provide a range of motion of external rotation which is different from the range of motion provided in the apparatus shown in FIGS. 8 and 9.

In this configuration, the forearm is oriented generally forwardly, and along the conventional line of sight of the user/patient 515, and the inflatable member 524 is located between the foam member and the forearm. It should also be noted that the foam block 550 could be a separate air bag 550, which could be inflated to a desired size and temporarily sealed.

Internal rotation could further be provided, by use of additional straps 525A and an additional inflatable air member 524A (shown in dotted line) to provide movement towards the body. These straps 524A would have one of their ends attached to the air bladder, and their other ends attached relative to the patient's body, preferably at about the right shoulder.

Therefore, internal and external rotation could be provided by the use of a pair of bladders as desired "IR" and 10 "ER".

It should be understood that the configurations described above which include the two oppositely located bladders may be used to provide "CPM", otherwise known as continuous passive motion.

Sixth Embodiment

FIG. 11

FIG. 11 illustrates a sixth embodiment 600 of the present invention, including a pair of horizontally-oriented straps 625U, 624L, an upper strap 624U located about the upper torso and approximate the armpit region, and the lower strap 625L being strapped about the lower torso of the body slightly upwardly of the belt region. Between the two straps is supported a foam pad, which fits generally underneath the armpit region of a particular arm of the wearer 615. An inflatable member 624 is located intermediate the underneath of the upper arm and the foam pad, such that inflation of the air bladder by the air pump 628 by the wearer 615 causes abduction of the shoulder. Although not shown, it should also be understood that a second inflatable member (not shown), with accompanying straps, could be used to cause movement in the opposite direction. A third shoulder-to-crotch strap 626 extends to underneath the groin region could also be used in order to provide support for pulling the scapula downwardly. This isolates motion to the glenohumeral joint (otherwise known as the arm/shoulder blade joint) as opposed to the acronmioclavicular joint.

Seventh Embodiment

FIG. 12

This embodiment of the invention comprises a device 700 which uses a substantially rigid structural member 701, an inflatable member 724, and straps 725 which connect the structural member 701 to the inflatable member 724. An additional hand strap 740 is provided to discourage movement of the inflatable member from its shown position to a position more towards the elbow. Another set of conventional straps such as 750 may be used to attach the structural member 701 relative to the upper arm.

As may be understood, by inflating the inflatable member 724, the straps 725 are drawn into tension and flexion of the elbow joint is provided.

Eighth Embodiment

FIG. 13

FIG. 13 relates the use a orthotic device 800 which include the use of alternating air flow to respective air bladders to cause range of motion in, for example, an ankle This is referred to as providing "continuous passive motion".

The device includes a hard shell boot 810, within which the lower leg, ankle, and foot of a patient is inserted. Two air bladders 824U, 824L, (although additional bladders could be used), are included within the boot. One air bladder is located, above the foot proximate the toe area, whereas the other air bladder is located beneath the sole of the foot proximate the toe area. The "upper" bladder 824U is separate from the "lower" bladder 824L, and the upper and lower bladders can be inflated and deflated separately, in order to provide an up and down motion of the foot, translating into an up and down motion of the ankle.

At least two types of flexion are intended to be provided under the present invention. These two types of flexion are plantarflexion, and the other type is dorsiflexion.

In an alternate embodiment of the present invention, two hinged flaps are also used within the boot cavity, one atop the foot and below the upper bladder, and the other below the foot and above the lower bladder. These two flaps correspond to the two bladders, such that inflation of the lower bladder pushes upwardly on the lower pivoting flap, causing upper flexion (dorsi) flexion, and increased air within the upper bladder, creates downward movement of the upper flap, causing the opposite type of flexion.

The two bladders are connected by two corresponding air lines, each of which are attached at their opposite ends to a common air source. Under one configuration of the present invention, the lines are alternatively filled and evacuated, causing the dual motion desired under the present invention.

Ninth Embodiment

FIGS. 14-16

This apparatus 900 includes a substantially flat base 901, an inflatable member 920, and a floating yoke member 930. The substantially flat base 901 includes a pair of upwardly directed holes 902 (as FIG. 14 is viewed) which slidably accept a corresponding pair of downwardly-directed feet 911 which extend downwardly and leftwardly at an incline from the inclined yoke plate 910.

Straps 925 are attached intermediate the upper end of the inclined yoke plate 910 and the inflatable member 920. A vertical anchor strap 935 is connected intermediate the upper end of the inclined yoke plate 910 and the base plate 901.

The inclined yoke plate 910 includes a tonguelike pad at 950 to provide a cushion as described below for the upper side of the foot. The tonguelike pad at 950 is located at the top of the yoke and can act as a type of "tramoline" pushing on the dorsum of the foot with a cushioning effect.

An air pump 990 with a quick release valve 991 is also included to inflate and deflate the air bladder within the fabric pouch of the inflatable member 920.

Such a yoke concept accommodates different sized feet, as a variety of feet can be slipped into the gap defined by angled yoke plate.

After the straps are properly adjusted to take out slack, the air pump 990 is used to inflate the inflatable member 920, tensioning the straps and providing a force on the calf of the leg of the wearer. This causes the ankle into desired dorsiflexion.

The downwardly-directed feet 931 do not bottom out in the holes 902, but instead are allowed to slide or "float" upwardly and downwardly therein. Since the straps are in tension, it may be understood that a force is applied to the top of the foot by the angled yoke plate 930 at the location of the tonguelike pad at 950. This causes the foot to be maintained in place due to pressure of the yoke atop the foot, instead of allowing the heel of the foot to lift from its location atop the base plate 901. A heel cup or stop 909 also may be used as shown in dotted line in FIG. 16.

The spherically shaped member 950 is configured to allow the base plate 901 to be put on a level supporting surface such as a floor surface such that the spherically shaped member 950 can provide a rolling pivot or rocking point about which the base plate 901 can rotate. This conveniently allows the lower leg to be maintained in a substantially consistent orientation while the forces within the apparatus cause the ankle of the foot into desired dorsiflexion. This can be quite convenient as it allows the user/patient to sit comfortably while undergoing the process.

Tenth Embodiment

FIG. 17

This device 1000 includes a substantially rigid structural member 1001 which resembles a open-backed "slipper" portion 1002 with a front vertical flange 1003 which extends upwardly from the top of the slipper portion and along the front of the shin of the wearer 1015. The wearer's front foot may be placed in the cavity of the slipper portion 1002, and an inflatable member 1020 may be placed behind the calf. This inflatable member is attached relative to the upper, free, end of the front vertical flange 1003 by one or more straps 1025.

After initial adjustment of the straps 1025, the inflatable member may be inflated by use of the air pump, causing the straps to be drawn into tension, and the calf to be pulled forward. This causes desired dorsiflexion of the ankle.

An optional strap at 1035 may be used to maintain the foot in place.

The spherically shaped member 1009 of the substantially rigid structural member 1001 is configured to allow the substantially rigid structural member 1001 to be put on a level supporting surface such as a floor surface such that the spherically shaped member 1009 can provide a rolling pivot or rocking point about which the substantially rigid structural member 1001 can rotate. This conveniently allows the lower leg to be maintained in a substantially consistent orientation while the forces within the apparatus cause the ankle of the foot into desired dorsiflexion. As noted above this can be quite convenient as it allows the user/patient to sit comfortably while undergoing the process.

It should be understood that this configuration 1000 may be used instead or in combination with the FIG. 14 configuration, if the yoke of FIG. 14 applies too much pressure.

Eleventh Embodiment

FIG. 18

FIG. 18 shows another orthotic device 1100 which can be used to provide dorsiflexion of the ankle This device 1100 includes a base 1101, a cuff 1102 fixed to the base, a selectively positionable foot plate 1103, an inflatable member 1120, and connecting straps 1125.

The selectively positionable foot plate 1102 is mounted to the base 1101 via a pivotable connection as known in the art, which allows for initial adjustment. However, it should be understood that when the orthotic device 1100 is in use, the pivoting connection is fixed such that the foot plate 1103 is fixed relative to the base 1101.

The cuff 1102 is fixed to the base, and allows for the lower leg of the wearer 1115 to slide therein as described below.

After initial adjustment of the foot plate 1102 and the straps 1125, the inflatable member 1125 is inflated, causing the straps to be drawn into tension. The inflatable member 1125 pushes down on the leg, namely the anterior aspect of the distal thigh, with the kneed flexed approximately 90 degrees. This causes the lower leg to move downwardly while being contained by the cuff 1102. This forces the ankle into dorsiflexion as the foot of the wearer bears against the foot plate 1103. Pressure may be relieved as desired.

FIG. 19

FIG. 19 is an illustrative view 1200 of a pair of exemplary limb members (such as an upper and lower leg, or such as an upper and lower arm), and how such members can be captured by the "three point" force configuration described above. Such a configuration provides an optimally efficient biomechanical application of force by positioning the inflatable member as far as possible from the pivoting point, whether that pivoting point be the joint (as shown in the FIG. 6), or the interface between the limb and the structural member (see FIG. 2).

Such a combination of the "three point" force configuration, the inflatable member, tensioning straps, and 3 structural member is submitted to be a significant improvement over the prior art as pressure is not provided across the joint, as might be provided by a simple "wrap" or the known cited art.

FIG. 20, 21

FIGS. 20 and 21 are pictorial and end views, respectively, of a forearm supination and pronation device 1300. This device 1300 includes a base 1301, right and left adjustable base flanges 1302L, 1302R, respectively, an inflatable member 1320, straps 1325, a retaining cuff 1327, and a glove assembly 1350 including a thumb retainer 1351. The base 1302 is configured to be stationary and to provide support for the other members.

The right and left adjustable base flanges 1302L, 1302R, respectively, are configured to the attached to the base, and to be adjustable. During use they are rigidly affixed relative to the base 1302.

The straps 1325 are positioned intermediate one of the base flanges and the rigid post member 1350.

The rigid post member 1350 is attached to the glove assembly 1340. This attachment can be temporary through VELCRO, snaps, or even a clothespin configuration. Alternately the post 1350 could be pivotally attached to the plate 1301.

The glove assembly 1340 can be attached to a user's hand by various means, but the invention contemplates the insertion of the hand into the glove assembly, which is snugged as desired by use of various straps or bands. The glove assembly includes a thumb retainer 1351 perpendicular to the longitudinal axis of the forearm.

By selectively adjusting the flanges and the straps supination and prontation of the forearm may be provided, while the glove twists atop the base plate 1301.

Although a glove assembly is disclosed above, it should be understood that the present invention also contemplates use of the device without a glove assembly. Such contemplation includes the use of some other means for attaching the post to the arm such that the longitudinal axis of the post is substantially parallel to the plane of the palm of the hand. Such an alternate configuration includes a strap which can fit around the hand across the palm and around the back of the hand, or a "clip" which can attach to the hand, or a "thumb sock", which can be used to contain the thumb relative to the post. However, it should be understood that for optimal biomechanical effect the thumb should be oriented generally alongside and parallel to the elongate post.

Options, Variations

It should also be understood that different fluids other than atmospheric air may be used, such as water, etc. Alternatively, hot or cold fluids, which may provide some therapeutic value, may likewise be used.

Various straps as known in the art may be used in order to maintain the outer boot in place on the wearer's limb.

It should be understood that under an alternative configuration according to the present invention, in order to provide an improved mechanical advantage, a boot may be used with a bent leg (providing an exposed upper horizontal surface) may be used. In such a configuration, the boot would include a strap which would go up and over the top of the knee, which is advantageous especially when providing the dorsi-type flexion of the ankle.

It should also be understood that the provision of air to the bladders according the present invention could be provided by automatic means, which may be advantageous in a long term type of treatment, such as the use of periodic inflation and deflation throughout a night time of wearing.

Furthermore, manual inflation and deflation for the provision of specific stretching of tissues may be provided by manual inflation and deflation of one of the bladders.

Finally, it may be understood that is not necessary that two bladders be used during a particular orthotic session; only one bladder may be used if only one type of motion is desired to stretch the limb against muscle tension.

Miscellaneous Comments

As noted above, a structural member may be used to provide structural support for various of the orthotic devices discussed herein. Such a structural device could be made of plastic, wood, metal, a metal/fabric sling, or other material(s) suitable to provide the needed support. It should be noted that although the structural support will need some type of stiffness to provide its support, it does not have to be perfectly rigid; some bending or deflection is possible and may be desirable.

CONCLUSION

Therefore it may be seen that the present invention provides a plurality of devices which provide improvements over known prior art othrotic devices.

While this invention has been described in specific detail with reference to the disclosed embodiments, it will be understood that many variations and modifications may be effected within the spirit and scope of the invention as described in the appended claims.

That which is claimed:

1. An orthotic device for manipulating a user's limb having a joint, said device comprising:
   a structural assembly comprising a first frame section and a second frame section; and
   a strap and bladder combination comprising:
      an inflatable member including an inflatable bladder configured for selective inflation and deflation and consequent expansion and contraction, respectively;
      a first flexible strap portion having two opposing ends, a first end configured for attachment relative to said first frame section, and a second end configured for attachment relative to said inflatable bladder at a first strap-to-frame attachment point; and
      a second flexible strap portion having two opposing ends, a first end configured for attachment relative to said second frame section, and a second end configured for attachment relative to said inflatable bladder at a second strap-to-frame attachment point, said second strap-to-frame attachment point being located relative to said first strap-to-frame attachment point such that said elongate space is intermediate said first and second strap-to-frame attachment points;
   said strap and bladder combination configured to be attached relative to said structural assembly by said first and second flexible strap portions such that said inflatable member is spaced from said joint and said limb can be positioned between said inflatable member and said structural assembly wherein a first gap is present between said joint of said user and said first frame section and a second gap is present between said joint of said user and second frame section, such that inflation and consequential expansion of said inflatable member causes both said first and second said flexible strap portions to be placed in tension such that said inflatable member exerts a force against said limb and causes both said first and second gaps to be reduced upon expansion of said bladder and causes said joint to move towards said elongate space between said frame sections.

2. An orthotic device for manipulating a user's limb having a joint, said device comprising:
   a structural assembly comprising a limb cradle portion configured to receive at least a first portion of said limb;
   an inflatable member;
   a flexible member interconnecting said structural assembly and said inflatable member such that a second portion of said limb can be inserted at a location between said structural assembly and said inflatable member and such that said second portion of said limb is in contact with said inflatable member while said first portion of said limb is in contact with said limb cradle portion; and
   an inflating device for inflating said inflatable member so that it increases in size, such that as said inflatable member is inflated, said inflatable member tends to push against said second portion of said limb such that said second portion of said limb is urged towards said structural assembly in such a manner as to result in flexion or extension of said joint.

3. The orthotic device as claimed in claim 2, wherein said inflatable member is attached relative to said flexible member such that when inflated, said inflatable member urges said limb towards said structural assembly and at least partially closes a gap between said limb and said structural assembly.

4. The device as claimed in claim 2, wherein said flexible member is elongate and includes two opposing ends and a medial portion therebetween, both of said ends are attached to said structural assembly, and said inflatable member is attached to said medial portion of said flexible member such that said inflatable member is captured between said flexible member medial portion and said limb during said pushing action.

5. The device as claimed in claim 2, wherein said flexible member comprises a plurality of flexible straps.

6. The device as claimed in claim 5, wherein each of said plurality of flexible straps is elongate and includes two opposing ends and a medial portion therebetween, both of said ends are attached to said structural assembly, and said inflatable member is attached to said medial portion of each of said plurality of flexible straps such that said inflatable member is captured between said medial portion and said limb during said pushing action.

7. The device as claimed in claim 2, wherein said structural assembly does not contact said joint.

8. The device as claimed in claim 2, wherein said limb is an arm and said joint is an elbow.

9. The device as claimed in claim 2, wherein said limb is a leg and said joint is a knee.

10. A method of using a structural assembly by a user in manipulating a limb having a joint, said method comprising the steps of:
- A) providing a structural assembly comprising a limb cradle portion configured to receive at least a first portion of said limb;
- B) providing an orthotic device for use in conjunction with said structural assembly, said orthotic device itself comprising:
  - 1) an inflatable member;
  - 2) a flexible member; and
  - 3) a device for inflating said inflatable member;
- C) positioning a second portion of said limb adjacent to said structural assembly;
- D) positioning said first portion of said limb adjacent to said limb cradle portion such that said first portion of said limb is supported by said limb cradle portion;
- E) attaching said inflatable member relative to said structural assembly by use of said flexible member such that said inflatable member is positioned in contact with said second portion of said limb such that said second portion is positioned intermediate said inflatable member on one side and said structural assembly on the opposite side; and
- F) subsequent to step "E," inflating said inflatable member such that said flexible member is drawn into tension and said inflatable member provides a force upon said second portion of said limb such that said joint of said limb moves toward said structural assembly in such a manner as to result in flexion or extension of said joint.

11. The method of claim 10, wherein during step "C", said second portion of said limb is positioned adjacent to said structural assembly such that said joint does not contact said structural assembly.

12. The method of claim 10, wherein during step "D", said second portion of said limb is positioned intermediate said inflatable member and said structural assembly on one side and said limb cradle portion on the opposite side.

13. The method of claim 10, wherein during step "F", said force upon said second portion of said limb urges said limb towards said structural assembly and at least partially closes a gap between said limb and said structural assembly.

14. The method as claimed in claim 10, wherein said limb is an arm and said joint is an elbow.

15. The device as claimed in claim 10, wherein said limb is a leg and said joint is a knee.

16. An orthotic device for manipulating a user's limb having a joint, said device comprising:
- a structural assembly comprising at least two elongate substantially rigid member portions, said elongate member portions spaced transversely a distance apart from each other;
- an inflatable member;
- a flexible member having a first and a second end, said flexible member interconnecting said elongate member portions and said inflatable member such that a portion of said limb can be inserted at a location between said structural assembly and said inflatable member and such that said limb portion is in contact with said inflatable member; and
- an inflating device for inflating said inflatable member so that it increases in size, such that as said inflatable member is inflated, said inflatable member tends to push against said limb portion such that said limb portion is urged towards said structural assembly in such a manner as to result in flexion or extension of said joint.

17. The device as claimed in claim 16, wherein said elongate member portions are substantially parallel to each other.

18. The device as claimed in claim 16, wherein said elongate member portions lie in a plane that extends substantially through the structural assembly, and wherein said limb portion is urged towards said plane when being urged towards said structural assembly.

19. The device as claimed in claim 16, wherein said first end of said flexible member is connected adjacent a first one of said elongate member portions and said second end of said flexible member is connected adjacent a second one of said elongate member portions.

20. The device as claimed in claim 16, wherein:
- said flexible member is elongate and includes a medial portion between said first and second ends of said flexible member; and
- said inflatable member is attached to said medial portion of said flexible member such that said inflatable member is captured between said flexible member medial portion and said limb during said pushing action.

21. The device as claimed in claim 16, wherein said flexible member comprises a plurality of flexible straps.

22. The device as claimed in claim 21, wherein each of said plurality of flexible straps is elongate and includes two opposing ends and a medial portion therebetween, said first of said ends is attached to a first of said elongate members, said second of said ends is attached to a second of said elongate members, and said inflatable member is attached to said medial portion of each of said plurality of flexible straps such that said inflatable member is captured between said medial portion and said limb during said pushing action.

23. The device as claimed in claim 16, wherein said inflatable member is attached relative to said flexible member such that when inflated, said inflatable member urges said limb towards said structural assembly and at least partially closes a gap between said limb and said structural assembly.

24. The device as claimed in claim 16, wherein said elongate members do not contact said joint.

25. The device as claimed in claim 16, wherein said limb is an arm and said joint is an elbow.

26. The device as claimed in claim 16, wherein said limb is a leg and said joint is a knee.

27. A method of using a structural assembly by a user in manipulating a limb having a joint, said method comprising the steps of:
- A) providing a structural assembly comprising at least two elongate substantially rigid member portions, said elongate member portions spaced transversely a distance apart from each other;
- B) providing an orthotic device for use in conjunction with said structural assembly, said orthotic device itself comprising:
  - 1) an inflatable member;
  - 2) a flexible member having a first and a second end; and
  - 3) a device for inflating said inflatable member;
- C) positioning said limb adjacent to said structural assembly;
- D) attaching said inflatable member relative to said structural assembly by use of said flexible member such that said inflatable member is positioned in contact with a portion of said limb such that said limb portion is positioned intermediate said inflatable member on one side and said structural assembly on the opposite side; and
- E) subsequent to step "D," inflating said inflatable member such that said flexible member is drawn into tension and said inflatable member provides a force upon one side of said limb portion such that said joint of said limb moves toward said structural assembly in such a manner as to result in flexion or extension of said joint.

28. The method of claim 27, wherein during step "C", said limb is positioned adjacent to said structural assembly such that said joint does not contact said structural assembly.

29. The method of claim 27, wherein during step "D", said limb is positioned intermediate said inflatable member on one side, and said structural assembly on the opposite side.

30. The method of claim 27, wherein during step "D", said inflatable member is attached relative to said structural assembly by attaching said first end of said flexible member to a first one of said elongate member portions and said second end of said flexible member to a second one of said elongate member portions.

31. The method of claim 27, wherein during step "E", said force upon one side of said limb portion urges said limb towards said structural assembly and at least partially closes a gap between said limb and said structural assembly.

32. The method as claimed in claim 27, wherein said limb is an arm and said joint is an elbow.

33. The device as claimed in claim 27, wherein said limb is a leg and said joint is a knee.

34. An orthotic device for manipulating a user's limb having a joint, said device comprising:
   a structural assembly;
   an inflatable member;
   a flexible member interconnecting said structural assembly and said inflatable member such that a portion of said limb can be inserted at a location between said structural assembly and said inflatable member and such that said limb portion is in contact with said inflatable member; and
   an inflating device for inflating said inflatable member so that it increases in size, such that as said inflatable member is inflated, said inflatable member tends to push against said limb such that said limb is urged towards said structural assembly.

35. An orthotic device for attachment to and for manipulating a user's limb having a joint, said device comprising:
   a structural assembly;
   an inflatable member inflatable from a lesser inflated mode to a more inflated mode;
   a retention member interconnecting said structural assembly and said inflatable member such that when said device is attached to said limb and said inflatable member is in said lesser inflated mode, a portion of said limb can be positioned at a location between said structural assembly and said inflatable member such that said limb portion being in contact with said inflatable member results in a gap between said limb portion and said structural assembly; and
   an inflating device for inflating said inflatable member so that it increases in size, such that as said inflatable member is inflated to said more inflated mode, said inflatable member tends to increase tension in said retention member, and said limb moves relative to said retention member such that said limb is urged towards said structural assembly wherein said gap is reduced.

36. An orthotic device for manipulating a user's limb having a joint, said device comprising:
   a structural assembly;
   an inflatable member configured to be inflatable from a lesser inflated mode to a greater inflated mode;
   a retention member; and
   an inflating device for inflating said inflatable member so that it increases in size, such that as said inflatable member is inflated to said greater inflated mode, said inflatable member provides a force upon one side of at least a portion of said limb such that said joint of said limb moves relative to said structural assembly in such a manner as to result in flexion or extension of said joint.

37. The device as claimed in claim 36, wherein said retention member comprises a plurality of flexible straps.

38. The device as claimed in claim 36, wherein said structural assembly does not contact said joint.

39. The device as claimed in claim 36, wherein said limb is a leg and said joint is a knee.

40. A method of using a structural assembly by a user in manipulating a limb having a joint, said method comprising the steps of:
   A) providing a structural assembly;
   B) providing an orthotic device for use in conjunction with said structural assembly, said orthotic device itself comprising:
      1) an inflatable member configured to be inflatable from a lesser inflated mode to a greater inflated mode;
      2) a retention member; and
      3) a device for inflating said inflatable member;
   C) positioning said limb adjacent to said retention member and said structural assembly such that said limb is generally parallel to said structural assembly;
   D) attaching said inflatable member relative to said structural assembly such that said inflatable member is positioned in contact with at least a portion of said limb; and
   E) subsequent to step "D," inflating said inflatable member such that said inflatable member provides a force upon one side of at least a portion of said limb such that said joint of said limb moves relative to said structural assembly in such a manner as to result in flexion or extension of said joint.

* * * * *